United States Patent [19]

Kiefer et al.

[11] Patent Number: 4,758,218

[45] Date of Patent: Jul. 19, 1988

[54] METHOD AND APPARATUS FOR GUIDEWIRE PLACEMENT OF CATHETERS

[75] Inventors: Patrick J. Kiefer, Green Bay, Wis.; James H. De Vries; Kenneth R. Jonkman, both of Grand Rapids, Mich.

[73] Assignee: DLP Inc., Grand Rapids, Mich.

[21] Appl. No.: 932,278

[22] Filed: Nov. 19, 1986

[51] Int. Cl.[4] ..... A61M 5/00

[52] U.S. Cl. ..... 604/53; 604/51; 604/184; 604/218; 604/231; 604/168; 604/900

[58] Field of Search ..... 604/53, 52, 51, 49, 604/57, 184, 218, 220, 231, 203, 158, 163, 168, 900, 95; 128/656-658, 772

[56] References Cited

U.S. PATENT DOCUMENTS

| | | | |
|---|---|---|---|
| 2,861,571 | 11/1958 | Sandhage et al. | 604/184 |
| 4,274,408 | 6/1981 | Nimrod | 604/52 |

*Primary Examiner*—Dalton L. Truluck
*Assistant Examiner*—Denise Whelton
*Attorney, Agent, or Firm*—Barnes, Kisselle, Raisch, Choate, Whittemore & Hulbert

[57] ABSTRACT

A percutaneous syringe assembly for use in the introduction of a guidewire into a blood vessel for the purpose of guiding a catheter into place. The syringe has a plunger with a central guide tube for the wire and a needle lumen for introduction of the wire into a blood vessel. A protective flexible container for a guidewire is attachable to the syringe plunger in a closed circuit with selective ends to be aligned with the central guide tube of the plunger to permit a J-end or a straight end of a wire to be introduced into a selected blood vessel.

5 Claims, 1 Drawing Sheet

62
60
52
50
44
62
22
40
43
20
42
24
64
29
28
26
32
30

FIG. 1
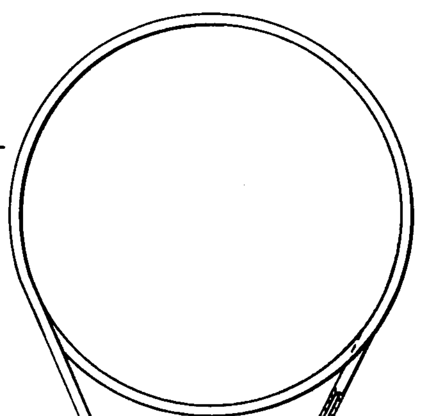
62
60
FIG. 2
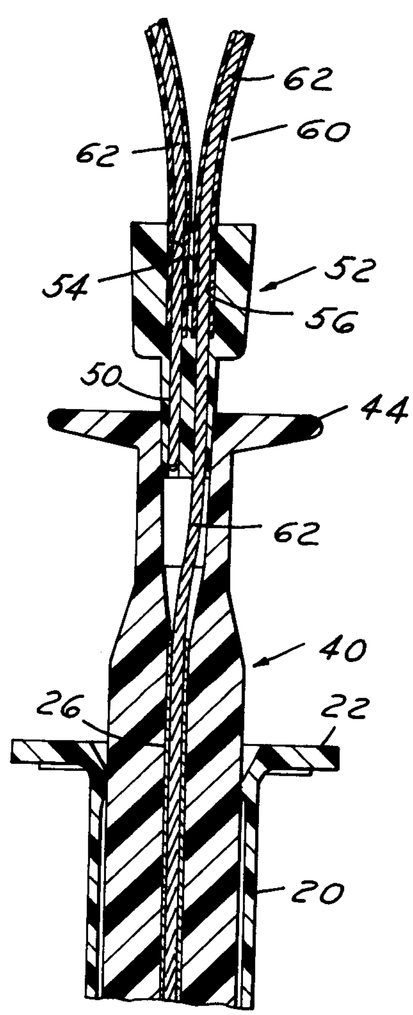
52
50
44
62
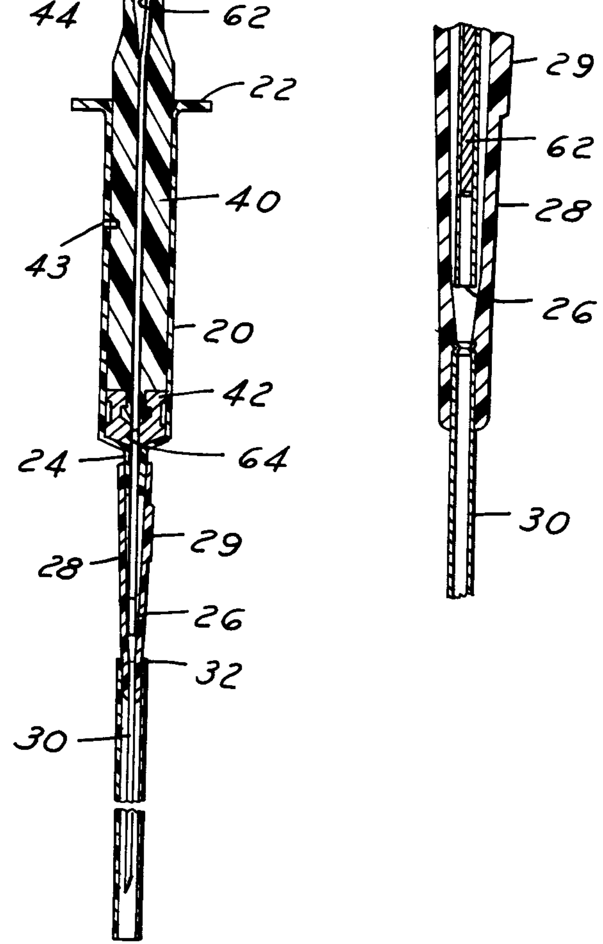
FIG. 3
29
62
28
26
30

METHOD AND APPARATUS FOR GUIDEWIRE PLACEMENT OF CATHETERS

FIELD OF INVENTION

Percutaneous guidewire placement in catheterization procedures and the like utilizing a hollow needle syringe.

BACKGROUND AND OBJECTS AND FEATURES OF THE INVENTION

Percutaneous sheath introduction sets are commonly used in the placement of Swan Ganz catheters, transvenous temporary pacing electrodes, subclavian dialysis catheters, and when a large bore intravenous catheter is needed for rapid administration of large volumes of fluid. A blood vessel is cannulated with a needle and a guidewire is inserted through the needle into the vessel. The needle is then withdrawn and a catheter is then placed into the vessel over the guidewire and the wire is then removed.

While successful catheterization of the vessel is usually achieved in most patients, multiple attempts per patient are sometimes necessary with a concomitant rise in complication rates. One cause of failure of catheterization is the dislodging of the needle from the vessel once puncture is identified by blood return in the syringe. This can result from movement of the needle while the syringe is being removed, when one attempts to stem the flow of blood from the needle hub or when the guidewire is being directed toward the needle for insertion. Once the needle is dislodged from the lumen of the blood vessel, the wire cannot be inserted.

It is an object of the present invention to combine the syringe and guidewire into one unit. This would have the advantage of lessening the chance of dislodging the needle from the vessel by eliminating the need to remove the syringe from the needle, to cover the hub of the needle to stem blood loss, and to reach for and direct the guidewire into the needle. The present system would also eliminate one of the possible sources of air embolism occurring during this procedure, a rare but disastrous complication of central venous catheterization.

In the present system, a hole is made in the middle of the plunger of the syringe and the flexible end of the guidewire is threaded through this hole so that a variable amount of wire is in the cylinder of the syringe. During the procedure, it is necessary for the syringe portion of the apparatus to be able to maintain both positive and negative (suction) pressures. Pressures are maintained by a rubber end of the plunger and a tapered luer fitting on the opposite end. When puncture of the vessel is successful, the seal at the luer fitting is broken, and the guidewire is advanced the desired distance into the vessel.

A U.S. Pat. No. 4,274,408, to Nimrod, issued Jan. 23, 1981, describes a method for guidewire placement and syringe for inserting a catheter guidewire into a blood vessel. This Nimrod disclosure relies on a ball or diaphragm to seal the opening containing the guidewire to enable the device to create both suction and pressure. The Nimrod plunger is used to break the seal or dislodge the ball seal.

In the present device, the guidewire is totally encapsulated and a fixed volume is trapped in the syringe. Consequently, no seal, as required by Nimrod, is needed. Thus, the present disclosure involves a simpler syringe construction which allows repeated uses since there is no sealing mechanism that is destroyed when the syringe is used. The present disclosure also reduces the possibility of contamination of the guidewire, and allows adaptability of either a straight end guidewire or a J-end as will be explained.

Other objects and features of the invention will be evident in the following description and claims in which the principles of the invention are set forth together with details to enable those skilled in the art to practice the invention, all in connection with the best mode presently contemplated for the invention.

BRIEF DESCRIPTION OF THE DRAWINGS

Drawings accompany the disclosure and the various views thereof may be briefly described as:

FIG. 1, a plan view of the assembled syringe and flexible wire sheath.

FIG. 2, an enlarged view of the manipulative end of the syringe plunger.

FIG. 3, an enlarged view of the needle end of the syringe.

DETAILED DESCRIPTION OF THE PRINCIPLES OF THE INVENTION AND THE MANNER AND PROCESS OF USING IT

With reference to the drawing, a syringe body 20 has an open end surrounded by a finger flange 22. The other end of the body is closed except for a central protruding tube 24 having an opening dimensioned to pass a metal sheath guide tube 26 fixed in the syringe plunger to be described. The protruding tube end 24 mounts a syringe needle hub 28 in the form of a tapered tube, the one end being slipped over the tube end 24 and the inner recess of the hub being tapered toward the distal end in which a hollow needle 30 is mounted. A small projection 29 orients the needle hub relative to the needle point for the convenience of the physician performing the procedure.

In FIG. 1, a needle protector tube 32 is frictionally held in the tapered hub 28, this to be removed in the percutaneous procedure.

A syringe plunger 40 in the body 20 has a resilient plunger tip 42 which has a slidable but sealing relationship to the inner wall of the syringe body. As described above, a metal guide tube 26 extends through the plunger and projects from the tip end of the plunger just short of the end of the tapered hub 28 when the plunger is at the lower end of the syringe body 20. The upper end of the plunger is narrowed for convenient manipulation and formed with a finger flange 44. The plunger, as described, has a central recess lined by the tube 26 for passing a guidewire and at the outer end the central recess is enlarged to receive a slightly tapered end 50 of a fitting 52. The body of this fitting has two parallel passages or lumens 54 and 56 spaced slightly apart. Both of these passages are open to the central passage in the plunger.

These passages receive in a tight sealed fit the respective ends of a flexible looped tube 60 which serves as a container for a flexible guidewire 62 shown in FIG. 2.

The plunger tip 42 has a central passage 64 which tightly encloses the guide tube 26 which will carry the guidewire 62.

The Operation of the Guidewire Insertion Syringe

The patient is suitably prepared in the area in which insertion is to be made and a local anesthetic is administered. A suitable needle such as an 18 gauge, 2½" needle is attached to the syringe tip or, preferably, the syringe is already equipped with a needle which is sterlized and protected by the removable tube 32.

The tube 32 is removed, the blood vessel is located, and the needle is inserted and the plunger 42 is withdrawn into the body 20. A stop 43 is provided to limit the withdrawal of the plunger to about 4 cc volume and to prevent withdrawal of the guide tube 26 beyond the protruding tube 24. While maintaining a vacuum on the syringe, the plunger is slowly withdrawn until blood flashes back into the syringe body. The fit of the wire in the guide tube 26 and the enclosed wire encapsulation allows this vacuum to be maintained.

If no blood flashes back, then the probe for the blood vessel has failed and another insertion must be made.

When the proper flashback of blood is achieved, one end of the container tube 60 is released and the enclosed guidewire 62 may be then fed manually through the syringe and needle into the vessel without removal of the needle. A guidewire with a J-shaped end, that is, an end which is preformed so that it takes a J-shape when unrestrained, may be used so that a rounded end moves into the vessel to prevent catching or tearing of the valves in the vessel.

It should be noted that the needle hub 28 is so dimensioned that a J-end of a guidewire will feed from the guide tube 26 into the needle 30. However, either the J-end or the straight end may be introduced by simply shifting the ends of the guidewire in the looped protector tube 60 and inserting the desired end into the plunger.

Once the guidewire has been introduced a proper distance into the selected vessel, the needle and syringe are removed leaving the guidewire in place. Then the appropriate catheter is fed into the vessel over the guidewire. When the catheter is in place, the guidewire can be readily removed and the catheterization procedure initiated.

What is claimed is:

1. A syringe assembly for percutaneous guidewire placement in catheterization procedures and the like which comprises:

(a) a hollow syringe body having a manipulative end and a needle hub end, (b) a plunger in said body having an inner end within said body with a slidable sealing relationship with the interior of said body and a central passage for the feeding of a guidewire and having an outer manipulative end outside said body, (c) a guidewire container tube having two open ends, having a guidewire therein (d) coupling means on the manipulative end of said plunger to removably receive said two open ends in a sealing relationship, such that when said two open ends of said container tube are received within said coupling means a seal is created at the manipulative end of said plunger said coupling means having a passage open to and in communication with at least one of said guidewire container ends and with said central passage, (e) a needle hub on the needle hub end of said body, (f) a needle on said hub having a lumen, said needle having a proximal end at the hub and a distal end at the outer end of the needle, whereby one end of said guidewire may be fed through said plunger and said needle lumen when one end of said guidewire container tube is removed from said coupling means on the manipulative end of said plunger and the seal of said container tube is broken.

2. A syringe assembly as defined in claim 1 in which a guide tube projects from the inner end of said plunger and is aligned with said needle hub.

3. A syringe assembly as defined in claim 2 in which said needle hub affixed to the hub end of said body has an interior bore leading to the proximal end of said needle to feed a guidewire from said plunger guide tube into said needle lumen, the said needle hub having sufficient length to accommodate said guide tube.

4. A syringe assembly as defined in 1 in which said coupling means comprises a fitting, said passage comprising two substantially parallel lumens which open into said central passage, each of said lumens having an outer end to receive and frictionally retain the respective ends of said guidewire container tube.

5. A method for guidewire placement of catheters which comprises:

(a) providing a syringe with a needle hub on one end containing a needle having a lumen, the syringe having a movable plunger with an inner end in sealing relation to the interior of the syringe and having an axial passage extending therethrough, said plunger having an outer manipulative end outside the syringe, (b) providing a guidewire container in the form of a double ended tube, (c) providing a recess means on the manipulative end of the plunger in communication with the axial passage, (d) associating the ends of the guidewire tube with said recess means to seal the axial passage and the guidewire container, (e) inserting the needle into a vessel and drawing back the plunger to create a blood flashback, and (f) releasing the guidewire tube to break the seal and feeding one end of the guidewire through the plunger and needle into the located vessel.

* * * * *